(12) United States Patent
Barham

(10) Patent No.: US 6,257,888 B1
(45) Date of Patent: Jul. 10, 2001

(54) DENTAL PRACTITIONER'S ACCESSORY

(76) Inventor: William L. Barham, P.O. Box 863, Mount Airy, NC (US) 27030

( * ) Notice: Subject to any disclaimer, the term of this patent is extended or adjusted under 35 U.S.C. 154(b) by 0 days.

(21) Appl. No.: 09/495,916

(22) Filed: Feb. 2, 2000

Related U.S. Application Data
(60) Provisional application No. 60/123,151, filed on Mar. 5, 1999.

(51) Int. Cl.$^7$ ..................................................... A61C 3/00
(52) U.S. Cl. .......................... 433/163; 433/49; 206/63.5; 224/217
(58) Field of Search ..................... 433/49, 163; 206/368, 206/63.5; 224/217, 218

(56) References Cited

U.S. PATENT DOCUMENTS

| 902,109 | * | 10/1908 | Powell | 433/49 |
| 1,139,942 | * | 5/1915 | Wightman et al. | 224/217 |
| 3,902,245 | * | 9/1975 | Wolf | 433/163 |
| 4,976,615 | * | 12/1990 | Kravitz | 224/217 |
| 4,988,296 | * | 1/1991 | Spncer | 433/163 |
| 5,368,482 | * | 11/1994 | Johnsen et al. | 433/49 |
| 6,036,490 | * | 3/2000 | Johnsen et al. | 433/163 |

FOREIGN PATENT DOCUMENTS

2595940 * 9/1987 (FR) ...................................... 433/49

* cited by examiner

Primary Examiner—Todd E. Manahan
(74) Attorney, Agent, or Firm—William J. Daniel

(57) ABSTRACT

An accessory for a dental practitioner during a dental procedure utilizing an instrument held in one hand is in the form of a miniature tray-like holder of tough sharp-point penetration resistant, stiffly resilient material, preferably a thermo-formable plastic, formed with a recess containing a flexible absorbent wiping medium for the instrument, such as one or more small elongated cylinders of conventional quilted dental padding or a flexible cellular foam, is anchored to the back of the opposite hand of the practitioner by means e.g. of a layer of adhesive carried on its underface and adhered to the back of the hand or resilient wings downwardly gripping a finger thereof. The recess is contoured to promote retention of the absorbent material therein The holder preferably also has a well for holding a small vial of tooth polishing paste adjacent to the wiping medium recess for ready access during polishing.

19 Claims, 2 Drawing Sheets

DENTAL PRACTITIONER'S ACCESSORY

This is a complete application of my PROVISIONAL application S.N. 60/123,151, filed Mar. 5, 1999, and currently pending.

INTRODUCTION

This invention relates to an accessory for dental practitioners for use in dental treatments, such as in endodontics, periodontal procedures, filling of teeth, cleaning or prophylaxis of teeth and so on, in which instruments or other devices are manipulated on the teeth by the practitioner with one hand, while the other hand is also positioned near the patient's mouth.

The accessory serves to expedite and facilitate certain repetitive operations performed with the instrument (and thus reduce the risk of repititive injury syndrome) by providing in an directly convenient and accessible fixed location on a back surface, i.e. opposite the palm, of the other hand, encased in a latex glove, of the practitioner and held there within a shallow miniature tray-like support, a medium cooperating during the treatment with the instrument in some fashion according to the type of treatment. The medium is a porous, absorbent flexible or yieldable wiping medium for removing from an operative edge of an instrument adherent matter collecting there during treatment. Such matter may be plaque, tartar, etc. during a cleaning or prophylaxis or blood, mucous and so on for a surgical or filling procedure. For dental prophylaxis, the holder may also advantageously carry a source of polishing compound as is usually applied to the teeth following cleaning. Alternatively, the wiping medium can serve for wiping from a dental mirror moisture fogging its surface.

BACKGROUND

In the practice of dentistry, it is necessary for most, if not all, procedures to manipulate within the patient's mouth various kinds of instruments to carry out particular operations according to the procedure being executed. One notable example of such an operation is the cleaning or prophylaxis of the teeth which should be periodically performed for proper dental hygiene to remove from the teeth plaque, tartar or calculus and other matter that collects on tooth surfaces especially in the vicinity of the gum line. This matter if left undisturbed can readily lead to the formation of dental cavities or worse conditions in the mouth, such as gingivitis and periodontitis.

As is commonly known, the cleaning procedure involves the scaling or scraping away of such matter that has adhered on surfaces of the teeth, especially those in the vicinity of the gum line and in intra-proximal regions. For this purpose, a dental hygienic technician or the dentist utilizes scalers, scrapers or picks shaped at their operative ends in various configurations designed to achieve the necessary scraping and cleaning action.

As the cleaning proceeds, these scalers or picks inevitably collect at their operative ends the plaque or other debris removed from the teeth. Consequentially, the end of the instrument must at frequent intervals be freed of this debris so that further cleaning can proceed readily without interference by the accumulated debris on the cleaning action of the instrument or obstruction of the field of view of the practitioner of the site being cleaned.

Typical dental chairs are equipped with instrument trays mounted on articulated and pivotable arms permitting the tray to be positioned at a location relative to the operator and patient affording convenient access to various instruments and the like placed thereon for use in cleaning. For ridding the end of the cleaning instrument of the accumulated debris, there is ordinarily placed loosely on this tray a paper tissue, gauze pad or other absorbent wiping material with which the operator can when needed wipe the instrument end free of adherent matter. Displacing the instrument from the patient's mouth to the tray or bringing the wiping material from the tray to the instrument end even when the tray is nearby involves rather awkward motions, and in any case either wiping motion takes a certain finite amount of time that when considered in the aggregate prolongs the prophylaxis. Also, the wiping tissue must generally be held stationary by the practitioner with the free hand while the other hand brings the instrument into wiping contact which causes the operator's attention to be distracted from the precise site in the mouth receiving treatment. Hence, when cleaning is resumed, the practitioner must recall the site at which the procedure was interrupted and begin again.

Of no less importance is the need to bring the instrument point into close proximity with the practitioner's unprotected hand holding the wiping medium, thereby introducing a significant risk of the occurrence of an "instrument stick", i.e. penetration of the skin of the holding hand by the point of the instrument. Certain dental cleaning instruments have quite sharp points or edges which are readily capable of penetrating the skin. Since the advent and wide-spread dissemination of "AIDS", i.e. "Acquired Immuno-Deficiency Syndrome", with its high fatality rate, much attention in the health care professions has been given to the avoidance of so-called "needle sticks", i.e. the penetration of the skin of medical professionals by the sharp points of hypodermic needles and the like used in the administration of medicaments to patients either at the time of administration or subsequently in the disposal of the needles.

It is now common knowledge that such needle or instrument sticks can result in the transmission to the medical professional of serious diseases carried by the patients, including AIDS, hepatitis A, B and C, and so on, all of which are known to be present in oral mucous as well as in blood serum and other bodily fluids. Thus, viruses or bacteria from dental patients can be bourn by debris, mucous, etc. collected on the ends of cleaning instruments and transmitted to practitioner by accidental pricking or scratching of the skin with potentially serious consequences. Any measure for reducing the opportunity for casual instrument sticks in the dental field would be highly desirable.

The same considerations with attendant risks obviously apply to other dental procedures including endodontic and periodontal procedures, filling of teeth and the like employing files, reamers, probes, drills and other instruments which become coated with mucous or blood during the procedure and likewise require wiping or cleaning from time to time.

In a less serious vein, it is frequently necessary for the practitioner to hold the handle of an angled mirror in the "other" hand while the "one" hand is manipulating an operative instrument in order to achieve through reflection a better view of the site in the mouth being treated. Such mirrors inevitably collect moisture and "fog over" from the high humidity environment of the mouth and require periodic wiping to restore a clear view. Up until now, the mirror surface has been wiped in basically the same manner as for working instruments (other than the difference in hands) which interrupts the concentration of the practitioner and consumes valuable time. Here also, it would be advantageous to have a wiping medium available in an immediately accessible location.

OBJECTS OF THE INVENTION

An object of this invention is to provide a porous, absorbent yieldable wiping medium for the cleaning an edge or surface of an instrument employed in dental prophylaxis or other dental procedures, which medium is contained in a small capsule-like or tray-like holder anchored in a fixed location on the upper or back side of the hand (encased in a latex glove for protection) of the practitioner opposite from the hand gripping the particular instrument to be cleaned. Because both of the practitioner's hands will ordinarily be directly proximate to the patient's mouth, one holding an operative instrument and the other a mirror, only a slight displacement of the instrument to be cleaned is required to bring the instrument part needing cleaning into wiping contact with the medium for freeing that part of the unwanted matter. This distance of a few inches at most contrasts with the one or more feet of distance at an absolute minimum separating the patient's mouth from the conventional instrument tray, with consequential maximum efficiency of motion and saving of time.

Another object is the provision of a wiping medium for cleaning the surfaces of dental instruments at a site as close as possible to the mouth of the patient to thereby lessen the risk of repitive motion injury.

An additional object is the provision of the wiping medium within the holder in a restrained condition resisting wiping contact by the instrument to be wiped wherein the medium is retained within a recess formed in the holder and preferably shaped to generally conform to the dimensions of the wiping medium.

Another object is to provide for the wiping medium a holder that is made of tough, preferably but not necessarily plastic, material substantially impervious to penetration by sharp objects and, moreover, encloses the wiping medium within a wall tending to prevent any sharp point or edge of the instrument from escaping from the confines of the holder while being cleaned.

A further object is to provide within the holder a wiping medium which is preferably of well defined structure and texture for efficient removal of collected matter on the instrument end and for secure enclosure within the recess of the holder.

Another object is to provide a small holder for one or more small pieces or wads of fibrous batting suitable for wiping dental instrument edges or surfaces which holder can be securely anchored on the upper side of one hand of the dental practitioner, which hand may be enclosed in a latex glove for therapeutic protection.

Yet another object is a wiping medium holder as described having on its undersurface an adhesive layer capable of adhering to the surface of a latex or vinyl glove.

Another optional object of the invention is to provide additionally in the holder a vial of conventional dental polishing compound in close proximity to the wiping medium so that the polishing compound is equally accessible to the polishing bristles applied to the teeth surfaces for final polishing and the motions involved in shifting a cleaning instrument to the wiping medium and a polishing brush to the polishing compound are virtually the same.

A still further object of the invention is a small holder for containing wiping medium formed as short elongated pieces of fibrous cotton padding, preferably in cylindrical shape spirally bound with filament for coherency and integrity, wherein the holder provides for receiving the padding pieces an elongated recess which is curved laterally to apply to the pieces a lateral stress resisting their inadvertent removal.

Yet another object is the provision along at least one side of the mouth of the recess of an inwardly directed lip to aid in retaining the pieces of wiping medium in place.

As an alternative, the wiping medium may be intended for wiping the surface of a dental mirror when fogged within the patient's mouth and for this purpose, the wiping medium can be constituted of a polymeric foam material, preferably hydrophilic in nature.

BRIEF DESCRIPTION OF THE DRAWINGS

Illustrative embodiments of a wiping medium holder according to the invention are shown in slightly enlarged fashion in the accompanying drawings in which.

DETAILED DESCRIPTION OF THE INVENTION

Figure 1:
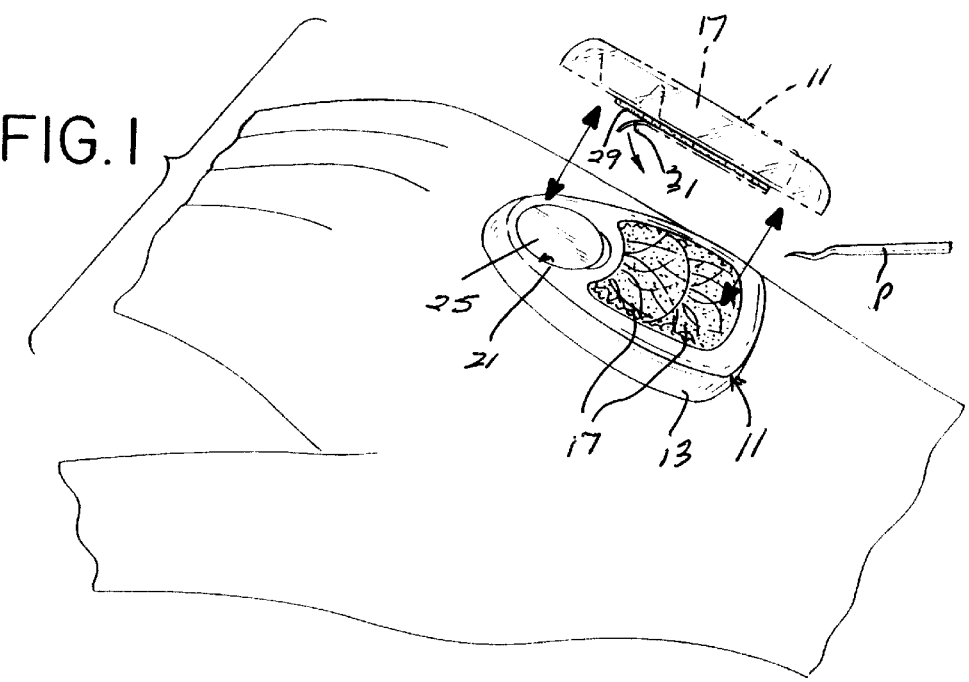
FIG. 1 is a perspective view of one embodiment of a wiping medium holder according to the invention showing in solid lines the holder in operative position anchored on the back of one hand of the practitioner and in broken lines in position for mounting, the two positions being connected by directional arrows indicating how the mounting is effected.

According to the invention, a small capsule-like or miniature tray-like holder preferably constructed of a thermoformable plastic is deformed to the desired configuration for holding a wiping medium for cleaning the end or surface of a dental instrument. The holder is adapted to be mounted by various means on one hand of the dental practitioner performing on a patient a dental procedure such as cleaning or prophylaxis which is opposite to the hand utilized for manipulating an instrument during the procedure. The opposite hand in question during the procedure may serve for the most part to hold and position a small mirror carried, as in well known, on one angular end of a rod-like handle with which the practitioner is able to observe otherwise obscured surfaces of the teeth to be treated, The handle of the mirror is gripped with the fingers of the hand in question, leaving the upper surface of that hand, and the appurtenant fingers, free and easily accessible. The holder is anchored generally on the back side, i.e. opposite the palm, of the selected hand or, alternatively on the back side of selected finger of that hand.

The shape of the holder is designed to contain a wiping medium for contact with the part of the instrument to be cleaned. Since the opposite hand in holding the mirror tool is already immediately adjacent the patient's mouth, location of the wiping medium holder on an upper surface of that hand positions the holder and the medium carried thereby closely proximate to the "working" hand of the practitioner. When a part of the operative instrument collects matter such as debris scraped from the patient's teeth or mucous or blood, it can be brought against the wiping medium to clear the matter with a short and quick wiping or sweeping motion and returned to the treatment site with minimum interruption of the procedure and minimum inconvenience to the practitioner.

Various configurations are possible for the holder; two of these are illustrated in the drawings but others are readily imaginable, some of which may be mentioned in the following detailed description while still others will be immediately suggested to one skilled in the art of dental hygiene.

Figure 2:
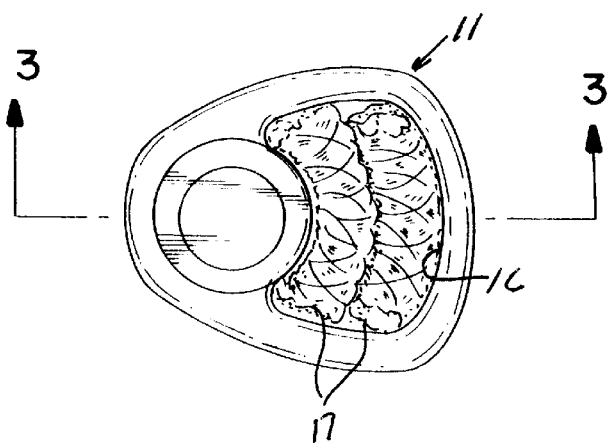
FIG. 2 is a top plan view of the holder embodiment of FIG. 1.
Figure 3:
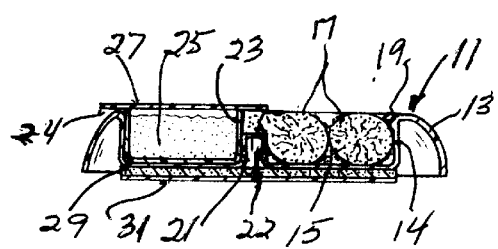
FIG. 3 is a cross-sectional view taken along line 3—3 of FIG. 2, showing inter alia on the underside of the holder an adhesive anchoring layer by which the holder is affixed to the upper side of one of the practitioner's hands, gloved as shown.

The first embodiment of FIGS. 1–3 employs an adhesive mode of attachment of the holder upon the back of the practitioner's hand. In the perspective of FIG. 1, the holder is mounted upon the right hand of the practitioner, who is assumed in this instance to be manipulating an operative instrument designated P in the other, i. e. left hand, not shown. Obviously, mounting the accessory upon the left hand is equally possible, depending upon which of the practitioner's hands is employed for manipulating the operative instrument. The practitioner's hand in keeping with modern precautionary measures will ordinarily be encased in a latex or vinyl glove; however, where circumstances permit the glove to be dispensed with, adherence of the holder to bare skin is an option.

The holder for the wiping medium takes the form of a small capsule-like or miniature tray-like flat receptacle formed preferably of a thermo-deformable or moldable thin tough flexible plastic sheeting as is routinely utilized at the present time for a variety of packaging purposes, such as pre-packaged bakery goods, small electronic devices, and many other small items. The type of plastic used can be varied as known in the art. Polyacrylates are one option, and polypropylene is another. The sheeting is preferably clear or slightly translucent, as shown, with a finely divided filler, such as talc, but could equally well be opaque or even colored with appropriate filler material. Any conventional thermo-molding technique can be employed, including blow-molding or vacuum-forming with a mould of the appropriate contour, either negative or positive to suit the selected molding technique. It need hardly be mentioned that the holder can be made by direct or injection molding of the plastic heated to a flowable condition.

In lieu of plastic, other materials can be substituted such as relatively dense paper-mache, as used for egg cartons, card-board or thin inexpensive metal sheeting e. g. of aluminum. Indeed, virtually any dense reasonably tough and durable sheet material that preferably is capable of withstanding a reasonable degree of penetrating force from sharp points or edges is suitable in principle for constructing the holder.

In FIG. 1, the holder in entirety is designated 11 and when viewed in plan is of generally triangular shape with rounded corners to give a pleasing design and good economies of material consumption. However, the plan shape is immaterial from a functional standpoint and can changed almost without limit, including rectangular, square, round, oval, irregular, etc. As can be best seen in the cross-section view of FIG. 3, the edge margins of the raw sheet or blank are deformed with downwardly directed side walls as at 13, to impart a suitable thickness thereto. These walls can be essentially perpendicular to the plane of the sheet or, as shown, inclined at an outwardly sloping angle thereto, An interior portion of the triangle spaced slightly from the side walls 13 is deformed downwardly to create depression or recess 15 having inner side walls 14 for containing a wiping medium generally designated 17. The outer side walls 13 do not contribute any essential function and could be eliminated if preferred. However, their presence results in double parallel walls defining a downwardly-opening re-entrant channel around the holder periphery which imparts thereto enhanced stability, strength and resistance to torsional stresses. Moreover, a flange (not shown) can project laterally from the peripheral edges of side wall 13 for adherence thereto of a protective cover sheet of acrylic film or the like.

In the embodiment of FIG. 1, the bottom or floor of recess 15 is flat and its depth is preferably slightly less than the vertical projection of outer side walls 13 for a purpose to be explained although they could have the same vertical extent if desired.

The wiping medium 17 can be virtually any flexible absorbent mass adapted to receive the matter to be removed from the instrument and suitable for packing into recess 15, such as cotton wadding or padding, woven or non-woven gauze, foam, sponge or the like, but is preferably in a defined tubular form, i.e. short elongated cylinders or rolls, best seen in FIG. 3. These cylinders are preferably quilted by dual, i.e. in both directions, spiral windings with fine filament, as suggested at 18 in FIGS. 1 and 2, to maintain their strength and integrity.

The lateral dimensions of recess 15 are basically governed by the nature and size of the selected wiping medium. For the preferred tubular (roll) form of medium, recess 15 is generally elongated in one lateral direction (more or less perpendicular to the direction of the section line 3—3) for a length selected to match the desired length of the tubular cylinders of padding 17. It will be understood that by "generally elongated" is meant that the recess is extended about two or possibly three times its width or enough to accept the length of the rolls of cotton padding as supplied. The orthogonal dimension of recess 15 (parallel to section line 3—3) depends upon the number and diameter of the quilted tubular cylinders and corresponds as shown to twice a single cylinder diameter to thus accommodate two such cylinders of padding (or enlarged for more as desired). Mutiple rolls of the padding lie generally parallel within the recess.

While cotton padding is a useful and available wiping medium, other fibrous or porous yieldable absorbent material can be substituted including bodies of synthetic fibers similar to cotton padding 17, masses of sponges or foams and so forth. The material should ordinarily absorbent for hydrophilic liquids given that oral fluids such as mucous and blood are water-based.

Preferably for one embodiment, the invention makes use for the wiping medium of a product used for other purposes in dentistry. In the filling of cavities and other remedial procedures, tubular quilted cotton padding (cotton dental rolls) of roughly one and one-half to two inches in length and about three-eights to one-half inch in diameter are often placed between the gum area of the tooth receiving treatment and the soft tissues of the inner surfaces of the cheek or the tongue. In this way, the soft tissues adjacent the treatment site are displaced away from possible painful contact by the dental drill or other equipment being used. This tubular padding is ideally suited as the wiping medium of the invention and is preferred for use in instrument-cleaning situations.

The number of pieces of such tubular padding 17 provided for cleaning, and consequently, the width of recess 15 containing the same and, if need be the area of the holder as a whole, can vary. Conceivably, a single piece might suffice but since the padding is fairly small and inexpensive, the preferred number is two, as shown, or even three, if a larger wiping area is advantageous, but more than three, say four or more, could be employed if desired.

The depth of recess 15 should roughly correspond to the thickness of the tubular padding while its width should be such that the selected number of padding pieces fits tightly therein.

It is desirable to employ some measure to positively secure the tubular padding or other wiping medium within recess 15 and avoid any chance of the padding becoming accidentally dislodged during use. Small dots of adhesive along the bottom of the recess, not shown, would achieve this objective but preferably, the recess is itself shaped to this end.

As appears in the FIG. 1 embodiment, one effective measure for positive retention of the tubular pieces within the recess involves giving the recess as a whole a lateral curvature or arcuate configuration, as is clearly seen in the plan view of FIG. 2. Placing of the tubular padding in the curved recess imparts to the padding a lateral bend. As made, the cotton roll padding normally has a generally rectilinear or straight condition as supplied and thus exhibits an inherent resistance to bending, i. e. an "memory" to return to straight condition if deformed therefrom. Placing the padding in the holder in a curved condition consequentially subjects the padding to lateral forces arising from this "memory" which urge the padding into frictional engagement with the walls of the recess and act to retain the padding therein.

Although the just=described feature is usually sufficient for adequate retention of the padding cylinders in the holder recess, additional measures can be included if desired. As one such measure, a lip cam be provided on at least the elongated or outer side of the recess located adjacent its upper edge for projection interiorly in overlapping relation to the upper portion of the adjacent padding piece seated in the recess. Thus, long wall 16 of recess 15 is at its upper edge deformed inwardly into a rounded lip or protuberance, appearing in section in FIG. 3 at 19. In this way, the upper end opening of recess 15 has a lateral dimension (width) somewhat smaller than the "normal" lateral dimension of the recess measured elsewhere along its depth, the normal lateral thickness being selected to substantially equal the diameter of one padding roll multiplied by the number of pieces used.

Thus, when the padding rolls are inserted into the recess, one or all of them must undergo diametrical compression in order to pass the lips into the depth of the recess, after which they expand to full diameter and are thereby wedged in place. Since they cannot thereafter leave the recess without undergoing re-compression, they are retained quite positively in the recess.

A most desirable and preferred feature for the accessory of the invention is provision for a source of polishing compound or prophylaxis ("prophy") paste, e. g. pumice or the like. Normal practice in prophylaxis calls for polishing of the cleaned, i. e. scraped, teeth with a polishing compound such as pumice applied by a polishing brush attached to a rotatably driven instrument or "drill". To this end, in the narrow end portion of the triangular holder, adjacent its apex and opposite to long wall 16 of recess 15, a circular recess or well designated 21 in FIG. 3, can be formed to receive a small cylindrical vial 23 of the polishing compound 25. The size of well 21 is such that vial 23 fits snugly therewithin. The vials in question are commercially available and are supplied with a peelable metal or plastic foil 27 cover to maintain the compound in fresh condition and this foil 27 can be peeled away at the beginning of the polishing procedure to expose the body of the compound to be picked up by the polishing brush.

Such vials of polishing paste are already utilized in dentistry but in the past, they have often been placed on the instrument tray for dipping of the polishing brush during polishing. It is also known to mount vials of polishing paste on rings for placement on fingers of the opposite hand of the hygienist, a practice that achieves in xmall part the improvement in efficiency that the invention carries to a distinctly higher level. By virtue of the inventive combination of both wiping medium and polishing paste source at the same site of the opposite hand of the hygienist, the movement of the "working" hand of the hygienist between the treatment point within the patient's mouth and the common location of both wiping medium and paste source follows the same path. This repetitive motion in practice within a quite short period of time becomes instinctive, or second-nature, maximizing efficiency and safety. Obviously, the closer the spacing of the vial recess to the wiping medium recess, the better for this adaptation to take place.

In the FIG. 1 embodiment, the well 21 for the vial of polishing compound is closely adjacent to the short side of recess 15 and is separated therefrom by a narrow upstanding arcuate rib 22 formed in the holder which rib completes the circular shape of well 21 (or enough of it that the vial is held in place) at a reduced height equal to about ½ or so of the full thickness of holder 11.

As seen in FIG. 3, vial 23 as supplied has a laterally outwardly projecting flange or lip 24 around its upper edge, a part of which extends above the upper end of rib 22. The lateral projection of this flange is sufficient to overlap the adjacent margin of recess 15 and provide a lip along a portion of the short side of recess 15 partially overlapping the adjacent padding material in recess 15. The compression of padding 17 within recess 15 (to accommodate to the curvature of the latter) may be sufficient to cause the padding to slough over into the space between rib 22 and the overlying portion of flange 24, as suggested in the drawing.

It is entirely possible (but less preferred) for the spacing between recess 15 and well 21 for the polishing compound vial 23 to be increased to an extent that flange 24 of the vial no longer overlaps with the adjacent margin of the padding. In that case, rib 22 might better be made of full height and increased thickness and deformed inwardly into a lip similar but opposite to lip 19 on the outer long wall 16 of recess 15 to achieve the same function as flange 24. Conversely, rib 22 can be virtually eliminated over a central arc, say 25 to 30 degrees above and below section line 3—3, thus placing recess 15 and well 21 in full communication over this arc and achieving some simplification in molding requirements.

It is imaginable that either one of the above measures for reatining the padding in place within recess 15 would alone suffice but a combination of the two insures that the padding pieces cannot be lifted free of the recess solely by the wiping contact therewith of the cleaning instrument (partially shown in one form at P in FIG. 1). Dispensing with the lateral curvature of the recess in favor of a rectilinear recess, not shown, would allow the padding pieces to assume a straight line position in the straight recess and is one possible modification. In that case, with the bending stress absent, it might be advisable to enlarge the inner projection of the retaining lip 19 of the recess or otherwise deform the side walls of recess 15 to enhance retention of the padding, e. g. provide an exaggerated inner protuberance at one or more points along the length of one oir both of the opposite side walls of recess 15 overlying the padding pieces.

Use of a laterally curved recess 15 in the holder has a secondary benefit of allowing the adjacent sidewall 13 of the triangular holder to be correspondingly curved or rounded, as can be seen well in FIG. 2 and by similarly rounding the other side walls and corners of the holder, a pleasing design is achieved. Obviously, this design relates only to the attractiveness of the holder and not to its function and although desirable is not an essential feature.

A triangular shape for the holder is ideally suited for inclusion of the polishing compound vial since the circular shape of the vial conforms to the arcuate inside curvature of the recess 15, giving a neat overall appearance to the holder. However, with other holder shapes or even with the triangular shape, the vial can be equally well provided in other locations, as will be obvious.

For example, with modest enlargement of a triangular holder 11, the padding recess 15 could be formed adjacent one apex of the holder and a plurality, say two, three or more, of the vial recesses provided along an opposite larger side of recess 15 to accommodate multiple vials of the polishing paste. Different formulations of the prophy paste are available from different sources and different hygenists can have different preferences amoung them. With several different kinds of paste available in a single holder, such preferences can be satisfied.

The bottom walls or floors of both wiping medium recess 15 and polishing compound well 21 preferably extend in co-planar relation to together serve as a base for the holder and this base can carry some type of anchoring arrangement for mounting the holder upon the opposite hand of the practitioner. As shown, the anchoring means can take the form of a short strip 29 of double-sided adhesive tape such as is readily available in hardware or variety stores. This tape comes in rolls or strips and carries an adhesive layer covered on each of its adhesive sides or faces by a peelable film 31.

The tape strip 29 is adhered on one face to the exterior surfaces of recess 15 and well 21 of the holder by peeling away the film from one of its faces, thereby exposing the underlying adhesive surface for adherence to the bottom of the holder. The outer face of the tape remains covered by the film 33. By making the outer side walls 13 of the holder slightly deeper (by an amount approximating the thickness of the adhesive tape), than the interior walls defining recess 15 and well 21, as mentioned earlier, the outer face of the tape and extreme lower edge of side walls 13 can be essentially co-planer, giving the assembly a high degree of stability when in working position, The accessory is generally is supplied in the condition just described, as shown in FIG. 3, although it will be apparent that the adhesive strip could be furnished separately with instructions for assembly by the user. At the beginning of the procedure, the remaining film 31 is peeled away from the bottom face of the tape (see the dotted line position of the holder in FIG. 1) and the holder is then adhered to the back of the practitioner's gloved hand, as indicated by the directional arrows in FIG. 1. It has been found that the standard commercial type of double-sided adhesive tape exhibits excellent adherence for the surface of an latex glove but will also adhere to bare skin if needbe.

Alternatively, a coating of a suitable adhesive can be applied to the undersurface of the holder from a solution in an appropriate rapidly drying solvent or in liquid form by heating. The adhesive is in this instance selected to exhibit when dry tight adherence to vinyl or latex surfaces but little or no adhesion to a protective covering film or alternatively, reduced adhesion to other surfaces, in particular the plastic selected for the holder, e. g. when several holders are packaged together for sale. It has been found that an adhesive sold commercially as "Ailene's Tack It" by Duncan Glue Co. of Fresno, California, meets these cirteria. Another possibility is an adhesive activated by some liquid that can be applied either to the exposed surface of the applied adhesive coating or to the back of the gloved hand of the practitioner just before the accessory is positioned for starting treatment.

Figure 4:
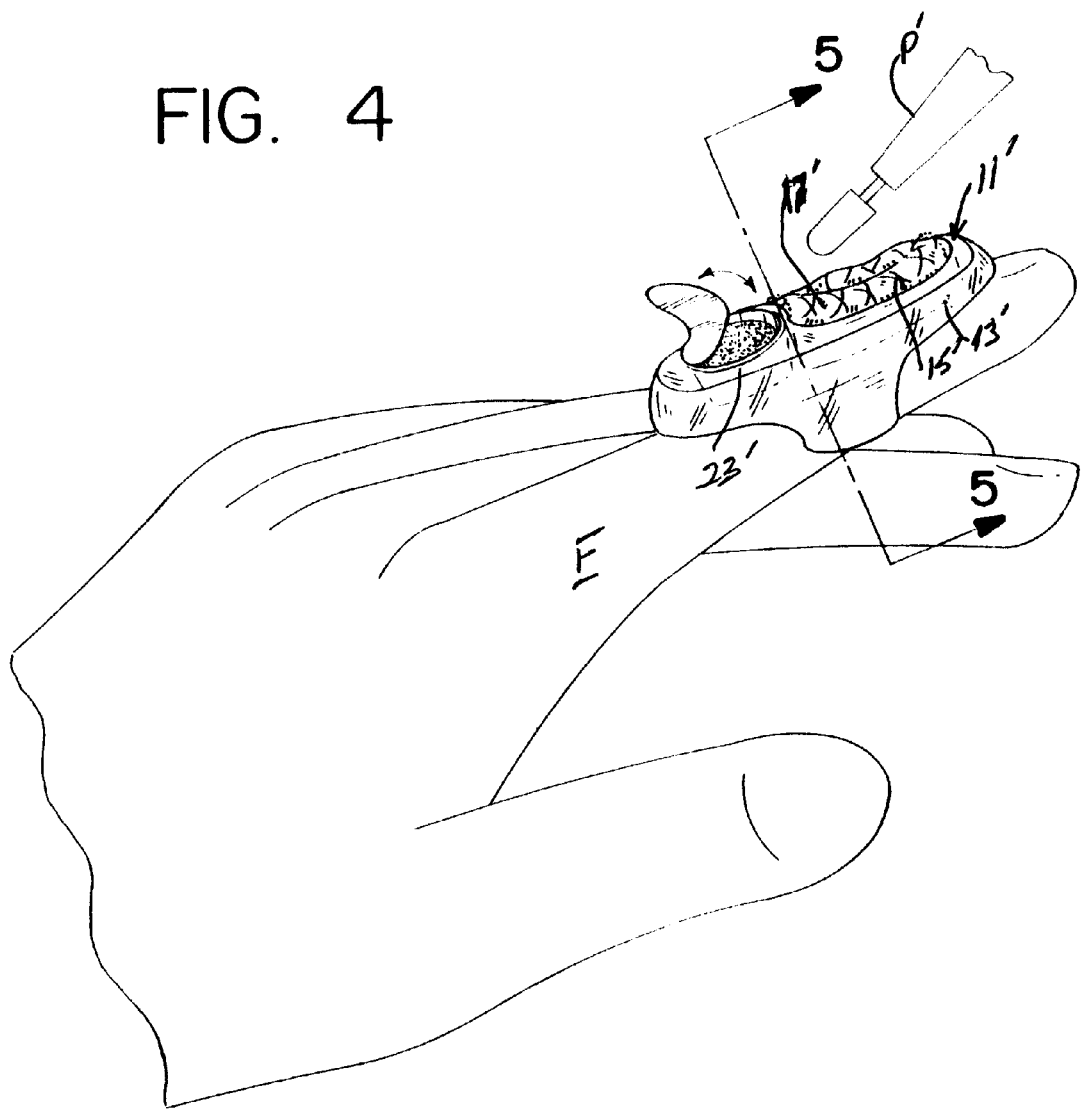
FIG. 4 is a perspective view of modified embodiment of a holder of the invention configured with downwardly depending flexible tabs for engagement with a finger of the practitioner.
Figure 5:
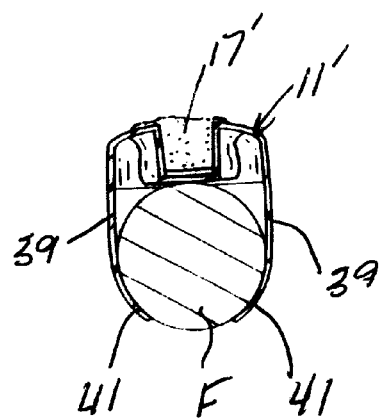
FIG. 5 is a sectional view taken along line 5—5 of FIG. 4.

Shown in FIGS. 4 and 5 is a modified form of the accessory the invention which is designed to be mechanically engaged on a selected finger F of the practitioner, such as the index finger, of the practitioner's opposite hand, i. e. from the hand working the scraper P' (seen partially in somewhat different form in FIG. 4). Here, the holder 11' has a narrow elongated configuration with downwardly curving side walls 13' to impart the necessary depth thereto. An elongated recess 15' stretches from one end of the holder about two-thirds of its length to contain the quilted wiping padding ropes 17' for wiping contact with cleaning scraper P'. While not visible in FIGS. 4 and 5, recess 15' is preferably slightly arcuately curved laterally of its length, as in the initial embodiment, and its long walls formed with inwardly projecting lips both for the same reasons as before.

Adjacent the other end of the modified holder 11', a cylindrical well (not seen as such in the drawings) is located for reception of the vial 23' of polishing compound. In the interest of reducing the length of the holder, recess 15 and the well can merge at their contiguous arcuate portions, as was also possible for the initial embodiment, leaving little or no separation therebetween. However, as before, the separation between the recess 15' and well could be increased and a defined rib (not shown) provided to distinctly separate the two.

For anchoring the holder 11', the bottom edges of the two long side walls 13' are extended downwardly in their central regions to constitute stiffly resilient finger-like appendages or "wings" 39 projecting downwardly from opposite sides of the holder body. The remote ends of wings 39 are bent toward one another, as at 41, the curvature being sufficient that the separation between the wings at their lower or free ends is less than the diameter of an average-sized finger. The operator's finger can be inserted between wings 41, as shown in FIG. 5, and the natural resilience of the plastic material forming the holders causes the wings to grip the finger F therebetween with sufficient force to hold the holder in place.

To ensure that the holder material has an adequate stiff flexible resiliency and sufficient toughness to avoid sharp-edge penetration, the gauge or thickness of the sheet from which the holder is molded can be varied as required.

If desired, the wiping medium of the invention (or the accessory in entirety) can be exposed to sterilizing (gamma) radiation to insure its sterility. Or the medium can be impregnated with a mild biologically compatible disinfectant or germicidal mouthwash that is effective to disinfect or reduce the biological activity of matter transferred from the teeth to the wiping medium. This can not only minimize the possibility of transferring disease-carrying matter to a different part of the patient's mouth but reduce the activity of biologically active material on an instrument point and thus provide added protection to the practitioner in the unlikely event of an "instrument stick".

In similar vein, the wiping medium can serve as an absorbent source for liquid medicaments that are often applied to the dental surfaces. Examples of such medicaments include topical anesthetics for reducing the sensitivity of gum tissue and per oxide agents indicated for treating periodontal disease. The wiping medium readily absorbs the desired treatment agent when introduced into the holder. So when the end of an instrument is pressed into the medium either incidental to a regular prophylaxis or deliberately in a special treatment step, that end becomes coated with the agent for application to the proper area of the patient's mouth.

It is even conceivable that two separate holders, or s single holder modified with two (or more) recesses, each containing its own wiping medium, could be affixed to the practitioner's hand, one for use during a regular prophylaxis, etc. and the other containing a desired medicament for some particular therapeutic measure called for by a individual patient. In this way, the practitioner can quickly and easily move an instrument end between the different holders at any given time and thereby function with maximum efficiency of motion and time and minimum loss of distraction.

A different utility of the accessory of the invention is for wiping the surface of a mirror frequently used by the practitioner during procedures carried out upon regions of the teeth not directly visible to the eye through the open mouth of the patient. Such mirrors are held in the hand opposite to that hand gripping the operative instrument and tend to accumulate on the mirror surface moisture "fogging" or clouding that surface and obscuring the reflected image. In this instance, the inventive accessory would be affixed to a back surface of the practitioner's hand holding the operative instrument. For this purpose, the wiping medium might be saturated with a defogging solution.

Thus, an accessory according to the invention could in many instances be anchored to the back surfaces of both of the practitioner's hands, one for wiping the instrument and the other for wiping the mirror surface whenever the need for either arises. And for procedures where cleaning of the operative instrument is of lessor concern but fogging of the dental mirror takes place, the accessory can be limited to merely the hand of the practitioner opposite to that gripping the mirror handle.

Reference has already been made to the possible replacement of the cotton wadding as the wiping medium with a flexible sponge-like or foam material which may be especially desirable for accessories intended to be used for wiping moisture from dental mirrors, This is not to imply that synthetic cellular materials such as foams are not suitable for cleaning the operative instruments because they are quite adapted to that end. The special utility of flexible foams for mirrow-surface de-fogging stems from the angular nature of most dental mirrors which introduces somewhat different considerations upon the contour of the wiping medium. Due to its angular orientation, a typical dental mirror cannot easily be swept across a generally flat wiping surface disposed on the back of the opposite hand. Of course, that hand can be rotated or tilted into an inclined position bringing the wiping medium surface into generally parallel relation to the angled plane of the mirror surface, or, alternatively, the handle of the mirror pivoted to achieve the same relationship. However, both of the latter motions are counter-intuitive and need a deliberate controlled motion.

Where the wiping medium is formed of a synthetic flexible foam, its body can be contoured or sculptured, e.g. by molding or shaping, to better cooperate with the mirror orientation. For example, a foam body could be given a rounded or dome-like shape projecting well above the top plane of the holder of the invention. Or a foam body could be shaped with an upwardly projecting "flange" or tongue or as a near equivalent, with a triangular cross-section providing an inclined wiping surface extending at least partially above the top of the holder. Arrangements such as these (and there are certainly other variations conceivable) can more easily receive the angled mirror surface when swept, for example, from a "far" position (beyond the accessory) to a "near" position.

With its location on the back of the operator's hand opposite from that manipulating an operative instrument, an accessory of the invention specifically intended for mirror-wiping purposes would find the presence of a vial of polishing paste superfluous. Hence, such a vial and the corresponding well can be eliminated or the recess simply left empty.

Various synthetic plastics or polymers can be utilized for a foam wiping material. The material should desirably be hydrophilic in order to possess absorptivity or compatability for water-based oral fluids such as mucous or blood. Cellulose as is commonly used for household sponges is hydrophilic and is one possibility; it has the disadvantage, however, of rather large and non-uniform cells. A superior cellular structure can result from a flexible polyurethane foam which can be hydrophilic in nature. A description of flexible polyurethane foams and techniques of their formation can be found in pp. 241–252 from Chapter 10 entitled "Polyurethane Foams" of the text "The Development and Use of Polyurethane Products" by E. N. Doyle, McGraw-Hill Book Co., Copyright 1971, among others.

As there explained in greater detail, such foams are prepared by reacting a polyisocyanate component with a so-called hydrogen donor, e.g. a polyol component, usually a high-molecular weight polyether, in the presence of a blowing agent and ordinarily a surfactant and a catalyst system. Cross-linkable reactants, having more than two reactive groups, are generally contra-indicated for flexible foams since they tend to yield rigid foams. By proper selection of these components flexible foams of quite uniform controlled cell size can be achieved. Similarly, the proportion of open vs. closed cells can be controlled, the degree of open cells influencing the degree of solvent absorption, and a hydrophilic nature compatible with oral exudates imparted to the foam.

For purposes of this invention, the polyurethane foams can be produced in large blocks and sub-divided into smaller pieces having the desired size and shape. Or the foam formulation could be injected into a mould of the desired size and shape and then removed and placed within the holder recess. More preferably, the foam body is generated "in-situ" within the appropriate recess of the holder. Thus, during assembly of the present accessories, a "one-shot" formulation of the reaction components can be injected in small quantity ("micro-injected") into the corresponding recess of the holder and allowed to foam there "in-situ", the upper surface of the resultant foam being shaped to the desired contour.

It has been found that "in-situ" foaming achieves sufficient bonding of the resultant foam with the inner surface of the holder recess so that no special measures, as described above, are necessary for adequate engagement of the foam within the recess.

Consultation with experienced producers of flexible polyurethane foams coupled, if need be, with some experimentation, readily leads to foams useful in the present environment. As one example, I have obtained satisfactory foams of this kind from North Carolina Foam Industries of Mount Airy, N.C.

Another less apparent utility for the accessories of the invention is as supports or carriers for small parts expected to be employed during a given dental procedure. As is well known, during the filling of teeth involving the use of drill bits or points replaceable inserted into the end of a rotary drill, different drill bits are often required. Where the practitioner can project in advance which kinds of drill bits are likely to be needed, the selected bits can be inserted via their small shanks into the foam of one of the present accessories anchored on the back surface of the hand opposite that gripping the drill. With the drill bits in this convenient location, they can be removed one by one from the foam and inserted into the drill end with only minimum interruption of the drilling action and without the dentist fumbling for the proper one on the conventional tray or, more likely, moving to a far-away cabinet to search for the correct bit there.

In this vein, I have found the present accessories to be most helpful in endodontic procedures, such as root canals. In the course of such procedures, it becomes necessary to "ream" out a root canal by means of tiny files or reamers. Due to the fineness of these reamers, they are difficult to pick up from the surface of a tray. However, they can be readily inserted upright into a foam wiping medium of the present accessory and held there until needed and then easily grasped with the fingers.

Where in the appended claims, reference is made to a "dental instrument" broadly without further differentiation, it should be understood that such reference is intended to apply to dental mirrors as well as to operatively functional instruments including scrapers, picks, drills and the like.

From the aforegoing disclosure and certain variations and modifications already disclosed therein for purposes of illustration, it will be evident to one skilled in the relevant art that the present inventive concept can be embodied in forms different from those described and it will be understood that the invention is intended to extend to such further variations.

What is claimed is:

1. An accessory for dental practitioners during dental procedures utilizing a dental instrument held in one hand comprising a shallow miniature tray-like support formed with at least one upwardly opening recess therein, said one recess containing a flexible absorbent wiping material adapted for repetitive contact during the procedure with the instrument, said recess being contoured to impart to said flexible material a lateral distortion from its undistorted configuration and thereby promote retention of said material in said recess, said tray-like support having on a side opposite said recess anchoring means adapted for anchoring said support on the back of the opposite hand of the practioner to expedite and facilitate said repetitive contact of the instrument with said medium.

2. The accessory of claim 1 in which said wiping medium is a body of a flexible hydrophilic polymeric foam which has a generally uniform cellular structure and is capable of absorbing oral fluids, said body being retained within said recess by lateral distortion imparted by the contour of said recess.

3. The accessory of claim 2 in which said polymeric foam is a hydrophilic polyurethane foam.

4. The accessory of claim 1 wherein said instrument has thereon a sharp edge capable of penetrating the practitioner's skin upon accidental contact therewith and said shallow recess is defined by a bottom wall and generally upstanding side walls on said support, said support being constituted of a stiffly resilient tough material adapted to resist penetration thereof by said sharp edge, whereby risk of skin penetration by said sharp instrument edge during periodic contact thereof with said flexible absorbent material is significantly reduced.

5. The accessory of claim 1 useful for dental prophylaxis employing a polishing medium wherein said support comprises at least one additional recess adapted to contain said polishing paste for application to the teeth during said prophylaxis.

6. The accessory of claim 5 in which said polishing medium is contained in a separate pre-formed circular vial and said additional recess is cylindrical to receive and retain said vial.

7. The accessory of claim 5 in which the first recess and said additional recess are situated in closely proximate relation to one another in said support.

8. The accessory of claim 1 in which said anchoring means comprises an adhesive layer carried on an undersurface of said support, said adhesive layer being adapted to adhere to a surface of a thin film glove encasing the practitioner's hand.

9. The accessory of claim 1 in which said anchoring means comprises a spaced apart pair of flexible wings extending from said opposite side of said support, said wings being adapted for cooperative downwardly grasping engagement with a finger of the opposite hand of said practitioner.

10. The accessory of claim 1 wherein said recess of said support is generally elongated in one direction and said flexible absorbent material comprises at least one elongated roll of absorbent cotton padding fitting within said elongated recess and retained therein by the contouring of said recess.

11. The accessory of claim 10 wherein said at least one cotton roll has a generally straight direction and said elongated recess is arcuately curved laterally of its long axis, said arcuate curvature forcing said roll therein into a curved condition serving to resist accidental removal thereof from said curved recess.

12. The accessory of claim 10 wherein said absorbent material comprises two elongated rolls of said absorbent material fitting in generally parallel relation within said arcuately curved recess.

13. The accessory of claim 1 wherein said recess of said support has a bottom wall and a plurality of side walls extending generally upwardly from said bottom wall, at least a portion of at least one of said side walls being deformed inwardly to compressively distort said flexible absorbent material against an opposite side wall portion and thereby promote retention of said material within said recess.

14. The accessory of claim 13 wherein at least said one side wall has along at least a portion thereof an internally protruding lip engaging a corresponding portion of said flexible material within said recess.

15. The accessory of claim 1 in which said flexible absorbent material comprises at least one coherent body of flexible absorbent fibrous material.

16. The accessory of claim 1 in which said flexible absorbent material comprises at least one elongated generally cylindrical roll of absorbent cotton padding.

17. The accessory of claim 16 in which each said elongated roll of padding is spirally wound externally with a filament to impart coherency thereto.

18. An accessory for dental practitioners during dental procedures utilizing a dental instrument in one hand, said accessory comprising a shallow miniature tray-like support formed with at least two upwardly opening recesses therein, one of said recesses containing a flexible absorbent material for wiping of said instrument and the other adapted to receive and retain a separate pre-formed vial filled with prophylactic paste for prophylactic application to the teeth, said vial having a laterally extending lip around its periphery and said two recesses being sufficiently closely proximate to one another that when said vial is present in said other recess, the lip of said vial projects over a portion of said flexible material to aid in retaining the latter in its recess, and said support has on a side opposite said recesses anchoring means adapted for anchoring said support to the back of the opposite hand of the practioner for easy access by said instrument.

19. The accessory of claim 18 wherein said one recess is elongated in one direction and is arcuately curved with a curvature generally parallel to an adjacent portion of the peripheral curvature of the lip of said vial, said flexible absorbent material in said one recess being generally correspondingly elongated and overlapped along an adjacent margin by the projecting lip of said vial.

* * * * *